United States Patent
Lvov et al.

(10) Patent No.: US 10,478,387 B2
(45) Date of Patent: *Nov. 19, 2019

(54) COATING OF CLAY MICRO-TUBES ON SURFACES OF HAIR AND NATURAL FIBERS

(71) Applicant: Louisiana Tech Research Corporation, Ruston, LA (US)

(72) Inventors: Yuri Lvov, Ruston, LA (US); Abhishek Panchal, Ruston, LA (US); Rawil Fakhrullin, Ruston, LA (US)

(73) Assignee: Louisiana Tech Research Corporation, Ruston, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,835

(22) Filed: Dec. 20, 2018

(65) Prior Publication Data

US 2019/0125637 A1    May 2, 2019

Related U.S. Application Data

(63) Continuation of application No. 16/037,206, filed on Jul. 17, 2018, now Pat. No. 10,166,175.

(60) Provisional application No. 62/550,926, filed on Aug. 28, 2017.

(51) Int. Cl.
*A61Q 5/10* (2006.01)
*A01N 43/00* (2006.01)
*A61K 8/26* (2006.01)

(52) U.S. Cl.
CPC .......... *A61K 8/26* (2013.01); *A61Q 5/10* (2013.01); *A61K 2800/43* (2013.01)

(58) Field of Classification Search
CPC .......... A61Q 5/10; A61K 8/4926; A61K 8/19; A61K 8/25; A61K 8/26; A61K 2800/42; A61K 2800/432; A01N 43/00; A01N 63/00; A01N 65/00; A01N 53/00; A01N 37/00; A01N 39/00; A01N 41/00; A01N 31/00; A01N 29/00; A01N 35/00
See application file for complete search history.

(56) References Cited

U.S. PATENT DOCUMENTS

| | | | |
|---|---|---|---|
| 10,166,175 B1 * | 1/2019 | Lvov | A61K 8/26 |
| 2008/0209645 A1 * | 9/2008 | Carrillo | C11D 1/008 8/137 |
| 2012/0207689 A1 * | 8/2012 | Konno | A61K 8/046 424/62 |

* cited by examiner

*Primary Examiner* — Eisa B Elhilo
(74) *Attorney, Agent, or Firm* — Jones Walker LLP

(57) ABSTRACT

A hair coloring mixture including a carrier liquid with alumino-silicate micro-tubes having a hair dye agent loaded into the lumen of the micro-tubes. The micro-tubes may be present in the carrier liquid in a concentration of between about 5 mg/ml and about 50 mg/ml, while the mixture will have a pH of between about 4 and about 7.

16 Claims, 3 Drawing Sheets

COATING OF CLAY MICRO-TUBES ON SURFACES OF HAIR AND NATURAL FIBERS

I. CROSS-REFERENCE TO RELATED APPLICATION

This application is a continuation of U.S. application Ser. No. 16/037,206 filed on Jul. 17, 2018, which application claims the benefit under 35 USC § 119(e) of U.S. Provisional Application Ser. No. 62/550,926 filed Aug. 28, 2017, both of which are incorporated by reference herein in their entirety.

II. BACKGROUND

Hair, protein filaments covering the skin of mammals, including humans, plays a pivotal role in skin protection, thermoregulation and touch sensing. Being one of the most visible human features, hair pigmentation can be modified using colorants and many commercial coloring formulations serve this cosmetic purpose. However, there is a contradiction in many conventional hair coloring techniques. On the one hand, the technique requires skin friendly aqueous dye solutions, and on the other hand, after application, the dye adsorbed on to hair has to be insoluble and as a practical matter, be able to survive at least 10 shampoo washes. These requirements are usually met with different chemical reactions involving the addition of $H_2O_2$ or other chemicals to color formulations, which are not healthy for hair and often cause allergic responses.

Another aspect of hair in humans and other mammals is that the hair may be affected by numerous diseases and parasites. Fungal diseases, mites, lice and fleas depend on hair serving as a shelter and breeding habitat. Although parasites such as lice are less common in industrial nations, they still pose a significant threat in developing countries, affecting millions. An effective therapy to eliminate these parasitic pests is required. However, a direct medical treatment is often difficult due to the complexities of providing sustain drug delivery onto hair.

Hair has a complicated chemical composition and its microstructure looks like attached flakes with narrow gaps called cuticles. The cuticles-cortex composite structure serve as binding sites for targeted interactions to adsorb drugs or dye. Lasting hair treatments like conditioners are focused at surface binding driven by charge or applied to the inter-cuticle spaces, in order to provide enhanced absorption into the cortex. Such formulations often disturb the natural chemistry of hair, causing dryness, oxidation and discoloration. An improved, longer-lasting, less damaging technique for applying both colorants and medicines to hair would be a significant improvement in the art.

III. SUMMARY OF SELECTED EMBODIMENTS

One embodiment of the present invention is a hair coloring mixture or dispersion. The coloring mixture generally includes a carrier liquid with alumino-silicate micro-tubes having a hair dye agent loaded into a lumen of the micro-tubes. The micro-tubes may be present in the carrier liquid in a concentration of between about 5 mg/ml and about 50 mg/ml, while the mixture will have a pH of between about 4 and about 7.

Another embodiment of the present invention is a biocide mixture for hair. The mixture also includes a carrier liquid with alumino-silicate micro-tubes disperse therein. However, the micro-tubes are loaded with a biocide and present in the carrier liquid in a concentration of between about 3 mg/ml and about 25 mg/ml, and the mixture has a pH of between about 2.5 and about 10.

Still other embodiments are described herein and/or will be apparent from the following detailed disclosure.

IV. BRIEF DESCRIPTION OF THE DRAWINGS

V. DETAILED DESCRIPTION OF SELECTED EMBODIMENTS

Figure 1A:
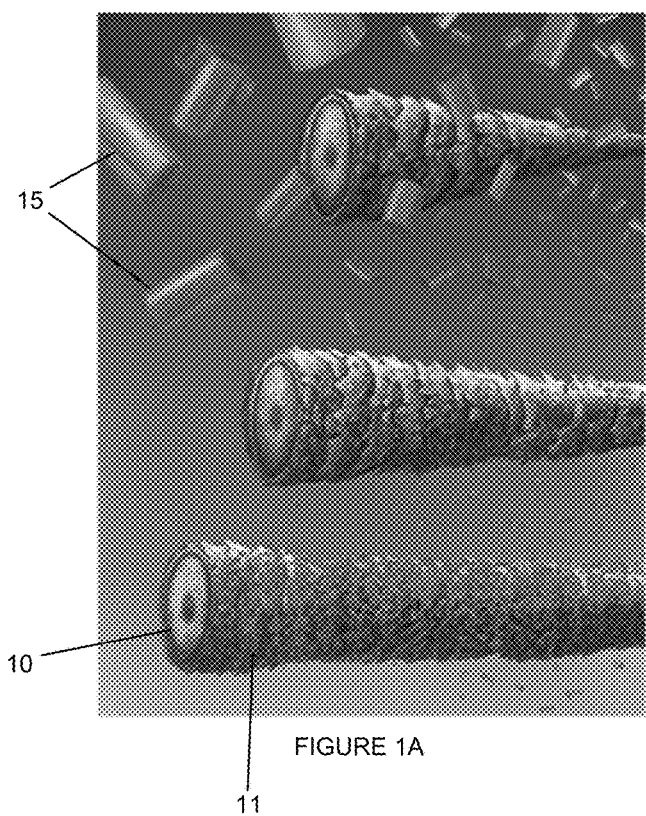
FIG. 1A is a conceptual illustration of the dye-loaded micro-tubes adhering to strands of hair.

One embodiment of the invention is a hair coloring mixture which generally is formed of a mixture (or dispersion) of a carrier liquid and alumino-silicate micro-tubes having a hair dye agent loaded into the lumen of the micro-tubes. In many examples, the carrier liquid is aqueous based, e.g., the carrier liquid is at least 51% water and could be at least any percentage of water between 51% and 99%. The carrier liquid can include any number of additives to the water base of the dispersion, e.g., surfactants, plasticizer, thickeners, preservatives, foam builders, sequestering agents, pacifying agents, clarifying agents, conditioners, anti-dandruff compounds, perfumes and/or artificial coloring agents. In one specific example, the carrier liquid is considered a "shampoo" if the liquid is at least 75% by weight water and includes a first surfactant, often sodium lauryl sulfate or sodium laureth sulfate, and a second or "co-surfactant," often cocamidopropyl betaine, to form a thick, viscous liquid. However, there could also be embodiments where the mixture is not aqueous based, e.g., contains less than 50% by weight of water. In certain preferred embodiments, the carrier liquid is free any substantial amount of organic solvent, with "substantially free" meaning less than 10% by weight (but also including any percentage less than 10).

The alumino-silicate micro-tubes can take on many forms, with one of the most common being naturally occurring minerals such as Halloysite ($Al_2Si_2O_5(OH)_4$) and sometimes may be referred to as "clay micro-tubes"). Halloysite forms as small cylinders (nanotubes) that typically have a wall thickness of 10-15 atomic aluminosilicate sheets, an outer diameter of 50-60 nm, an inner diameter of 12-15 nm, and a length of 0.5-10 μm. Their outer surface is mostly composed of SiO2 and the inner surface of $Al_2O_3$, and hence those surfaces are oppositely charged. The term "micro-tubes" includes any tubular material having micron level dimensions (e.g., the length dimension of the tube being under 1 mm), but more typically refers to tubulars having an outer diameter that is sub-micron and lengths under 100 microns, under 50 microns, or under 10 microns. There may be embodiments of the invention which employ micro-tubes which are alumino-silicate, such as halloysite and imogolite, or which are not alumino-silicate, such as sepiolite or cylindrite. All of the foregoing micro-tubes may be considered in the family of "clay" micro-tubes.

In many embodiments, the concentration of micro-tubes in the carrier liquid is between about 5 mg/ml and about 500 mg/ml or any sub-range there between. In certain preferred embodiments, the concentration of micro-tubes is between about 10 and about 50 mg/ml.

Similarly, in many embodiments, the dispersion (i.e., the combination of the carrier liquid and nano-tubes) will have a pH of between about 2.5 and about 10 (or any sub-range there between). In one example, the dispersion will have a pH range of between about 4 and about 8. In another example, acetic acid is included in the dispersion in an amount sufficient to establish the dispersion pH at between about 3.5 and about 5.5.

As suggested above, the micro-tubes in the hair coloring mixture will have a hair dye agent loaded into a lumen of the micro-tubes. The hair dye agent may either be a substantially water soluble (hydrophilic or polar) agent or a substantially water insoluble (hydrophobic or nonpolar) agent. Non-limiting examples of a hydrophilic hair dye agents may include Indigo carmine, Carmine, an Anthocyanin, pseudopurpurin, and Brasilein. Examples of an Anthocyanin may include pelargonidin, cyanidin, peonidin, delphinidin, petunidin, or malvidin. Similar non-liming examples of hydrophobic hair dye agents include Shikonin, Quercetin, Lawsone, Isorhamnetin, Curcumin, and Alizarin.

One example method of loading the micro-tubes with a (substantially) water soluble hair dye agent uses the dye Indigo carmine. The Indigo carmine dye is dissolved in 1 mL of DI water at a ratio of 4% by weight (i.e., 40 mg of dye) under sonication. 40 mg of halloysite is added to the dispersion and sonicated until a homogeneous dispersion is obtained. The dispersion is place under a low vacuum (e.g., at approximately 1 psi or less) for three cycles, one hour for each cycle. The halloysite is then thoroughly washed with DI water five time by centrifuging at 10,600 rcf for three minutes. The washed halloysite was then dried in a hot air oven at 60° C. This procedure produced a 6 to 8 weight percent dye loading efficiency, i.e., weight of dye with respect to the weight of clay micro-tubes. However, different procedures may be used and generally it is desirable to generate micro-tubes loaded to about 5 to 10 weight percent dye loading efficiency, but in other embodiments, the loading efficiency could be between 3 to 35 weight percent (or any sub-range in between).

One example method of loading the micro-tubes with a (substantially) water insoluble hair dye agent uses the dye Lawsone. It is preferable to modify the halloysite lumen surface to allow more ready binding of nonpolar molecules. The halloysite is modified with the anionic surfactant sodium dodecyl sulphate (SDS) by thoroughly dispersing halloysite nanotubes via sonication in a solution of SDS at 2 mg/ml with the weight ratio of halloysite:SDS being 1:1. Below the critical micellar concentration, SDS is in solution as linear chains and hence more likely to enter the 15 nm wide lumen of halloysite tubes. The halloysite-SDS dispersion is allowed to stir for 48 hours followed by centrifugation for 3 min at 1000 rpm. The absorption of SDS on positive alumina groups neutralize the positive charges and increases the net negative charge of halloysite tubes imparting greater ability to remain in dispersion. Halloysite microtubes which so are modified (halloysite-SDS) tend to remain as colloid, and the centrifugation helps to select such halloysites from supernatant and eliminate the precipitate of non-modified tubes. The selected supernatant is centrifuged at a higher speed and time of 5000 rpm, 20 min to separate out the halloysite-SDS. The separated halloysite is subjected to a series of washes with DI water to remove the excess surfactant until the washings possess the same surface tension as water. After four to five washings, the halloysite is dried overnight under vacuum.

To load the Lawsone dye, it is dissolved at a concentration of 45 mg/mL in a 1:8 (vol/vol) mixture of water and acetone. Typically, when loading dyes such as Lawsone, the dye is dissolved in a solvent/water solution which is at least 51% organic solvent. The SDS-treated halloysite is added to the saturated dispersion of Lawsone with the ratio of halloysite to Lawsone bring 1:1 by weight. The dispersion is stirred for 30 minutes and then subject to a vacuum for another 30 minutes. This one hour stir-vacuum cycle is repeated twice with the replenishment of solvent volume (i.e., by solvent without micro-tubes) to initial levels before drying off the solvent in a vacuum overnight. The excess dye is washed with the water-acetone solvent and separated by centrifugation. This procedure produced a 4 to 9 weight percent dye loading efficiency. However, different procedures may be used and generally it is desirable to generate micro-tubes loaded to 4 to 25 weight percent dye loading efficiency for dyes considered water insoluble. Organic solutions from solvents such as alcohol, chloroform, and acetone may be employed when loading the micro-tubes with insoluble dyes.

In many embodiments, it may be desirable to hydrophobize the outer surface of halloysite, for example to exploit the lipid character of cuticles. Halloysite in its pristine form is hydrophilic with a contact angle of ca. 16°. In one example, (3-Glycidyloxypropyl) trimethoxy silane or GTMS is the silane coupling agent that is coupled to the hydroxyl groups present at the halloysite surface. The choice of silane coupling agent includes but is not limited to 3-aminopropyltri-ethoxy silane (APTES), hexamethyldisilazane (HMDS) and octadecyltrimethoxy silane (ODTMS). Halloysite silanized to have contact angle of about 50° are prepared by sonicating 6 g of halloysite tubes, 8 g GTMS in 60 ml isopropanol for 30 min and then setting under a condenser to reflux for 72 hours at 85° C. The ratios and the choice of the silane agent and solvent can be changed to develop more or less hydrophobic halloysites. In many embodiments, it is desirable for the exterior surface of nano-tubes have a contact angle of at least about 30°. However, other embodiments may have contact angles as high as 120° and alternate embodiments could have a minimum contact angle of anywhere between 30° and 120°. In most embodiments, the surface modification of the micro-tubes is carried out prior to loading the lumens with dye.

A further embodiment of the invention is a method of coloring hair which includes the step of applying to the hair (e.g., massaging into hair as in normal hair washing) one of the above described hair coloring mixtures for at least one minute. The mixture may be left on the hair for longer periods of time, e.g., three to five minutes. After the desired application time, the mixture is rinsed out of the hair and the hair is allowed to dry as normal.

Figure 1B:
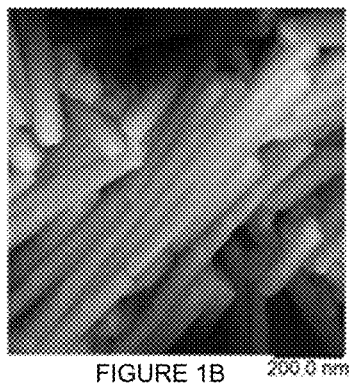
FIG. 1B is an atomic force microscopy (AFM) image of dried clay micro-tubes.
Figure 1C:
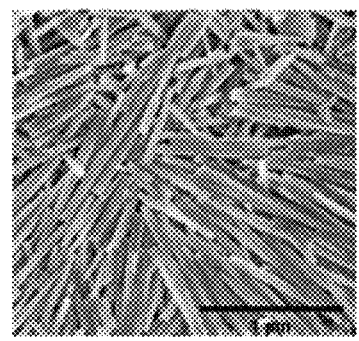
FIG. 1C is a scanning electron microscopy (SEM) image of dried clay micro-tubes.
Figure 2A:
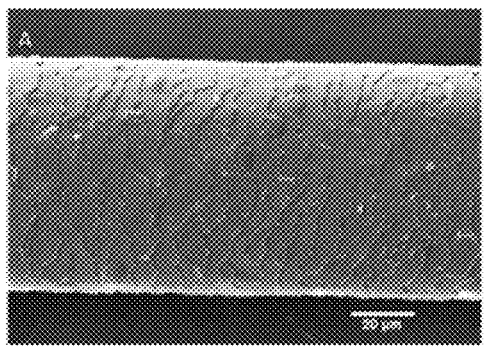
FIG. 2A is a SEM image of the pristine surface of a human hair.
Figure 2B:
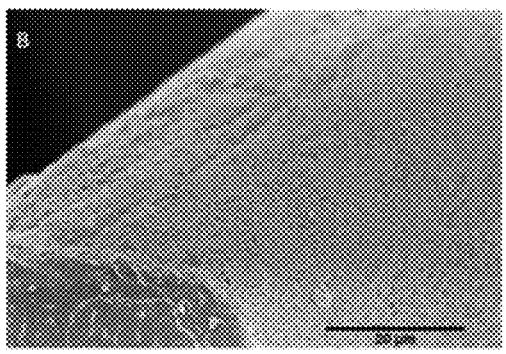
FIG. 2B is a SEM image of the human hair covered with clay micro-tubes.
Figure 2C:
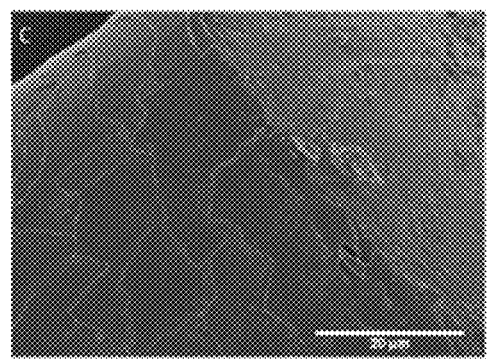
FIG. 2C is an enlarged view of the FIG. 2A image.
Figure 2D:
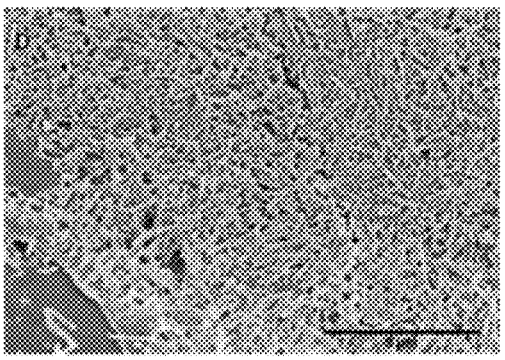
FIG. 2D is an enlarged view of the FIG. 2B image.
Figure 2E:
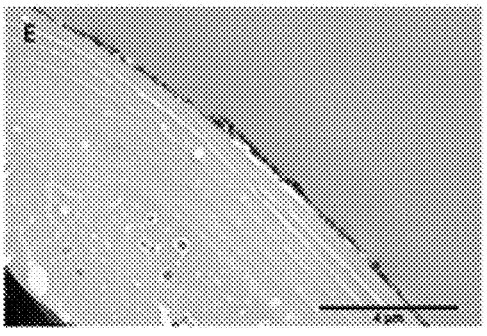
FIG. 2E is a transmission electron microscopy (TEM) cross-section image of a coated hair strand showing the darker layer of micro-tubes at the cross-section edge.
Figure 2F:
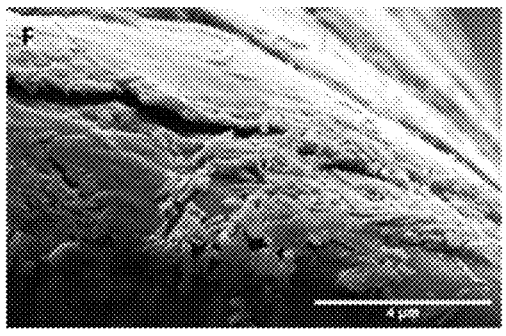
FIG. 2F is a SEM image of the area seen in FIG. 2E.

In many embodiments, the hair cuticles are the anchor sites for the halloysite micro-tubes. The micro-tubes assemble in and around the cuticles and then propagate further in the water based treatment. FIG. 1A illustrates conceptually strands of hair 10 in a micro-tubes 15 containing aqueous mixture. The micro-tubes 15 are shown anchoring to the hair cuticles 11 and propagating further along the hair strands 10. FIG. 1C shows a scanning electron microscopy (SEM) image of dried clay micro-tubes, while FIG. 1B shows a higher resolution atomic force microscopy (AFM) image of the dried clay micro-tubes. FIG. 2A shows a SEM image of the pristine surface of a human hair, while FIG. 2C is an enlarged view of the FIG. 2A image. FIG. 2B is a SEM image of the human hair after employing the above described methods to covered the hair with halloysite micro-tubes. FIG. 2D is an enlarged view of the FIG. 2B image. FIG. 2E is a transmission electron microscopy (TEM) cross-section image of a coated hair strand showing the darker layer of micro-tubes at the cross-section edge. FIG. 2F shows a SEM image of the area seen in FIG. 2E.

In many of the above examples, the hair coloring process results in a coating thickness of 3-5 µm formed by few layers of randomly attached micro-tubes. The micro-tube coating on the hair results in an increase of the surface roughness of the hair by at least 25%, and more commonly at least 30% to 50%. In embodiments where the pH is lowered to about 4.5 (e.g., with acetic acid), a significant advantage is provided as it aids in the swelling of the hair. Such hair swelling promotes initial anchoring of the micro-tubes by creating more inter-cuticle spaces.

Those skilled in the art will recognize the above described embodiments are applicable for almost any dye, including non-water soluble dyes which may be loaded into hydrophobized halloysite lumens, keeping the formulation natural and thereby preventing allergic reactions. Because in many embodiments the dye is not released from the nanotube, the disclosed formulations for hair coloring avoid direct contact of dye to the hair, replacing the currently accepted hair chemical modification process with the physical sorption self-assembly of micro-tubes. This approach may greatly widen a color palette for the hair care with the clay encapsulation of dyes which, for different reasons, are not acceptable for more direct exposure on human tissues.

A related embodiment of the invention is a hair dying kit which provides an extended shelve life for the hair coloring composition. This kit includes a first container having a volume of carrier fluid, the carrier fluid having a water content of at least 65%, but no significant concentration of dye containing micro-tubes in the carrier fluid. The kit also includes a second container having a weight of the micro-tubes with a hair dye agent loaded into the lumen of the micro-tubes. The micro-tubes in the second container are in a substantially dry state, allowing for the long term maintenance of the dye agent within the lumens of the micro-tubes. The weight of micro-tubes in the second container to the volume of carrier fluid in the first container is between 5 mg/ml and 50 mg/ml. When the consumer is ready to dye his or her hair, the micro-tubes can be added to the carrier fluid and the resulting mixture vigorously mixed (e.g., by shaking the first container) until the micro-tubes are thoroughly mixed in the carrier liquid.

Some embodiments may involve application of the dye containing micro-tubes to hair without a liquid carrier agent. For example, comparatively dry dye containing micro-tubes could be loaded in a conventional aerosol spray can and be applied to the hair as a comparatively dry pressure driven aerosol. Alternatively, the micro-tubes in a carrier liquid could be loaded in a spray can and applied as a generally wet aerosol. This aerosol technique may be even more applicable to micro-tubes loaded with biocides as described below. This will be especially true for micro-tubes loaded with anti-flea agents for application to pets, although the spray technique is also applicable to micro-tubes loaded with anti-lice agents for humans and other mammals.

Another aspect of the present invention is a biocide mixture for hair. As with the above embodiments, the biocide mixtures is formed of micro-tubes dispersed in a carrier liquid. The carrier liquid may be as previously described, but the micro-tubes will be loaded with a biocide. In certain embodiments, the biocide will be either an anti-flea agent or an anti-lice agent and the micro-tubes will be present in the carrier liquid at a concentration of between about 3 mg/ml and about 25 mg/ml (although in other embodiments, the concentration could be in any range between 3 mg/ml and 500 mg/ml), while the mixture has a pH of between about 3.5 and about 7.5. An "anti-lice agent" can be any compound currently or in the future approved by drug regulatory agencies for the treatment of lice (with a similar definition applying for anti-flea agent and hair dye agent).

In one embodiment, the anti-lice agent or (pediculicide) will be one or more from the group consisting of Permethrin, IR 3535, Saltidin, Picaridin, Cinerin, and N,N-Diethyl-meta-toluamide (DEET). In another embodiments, the biocide will be an anti-flea agent and in preferred embodiments, one or more of the anti-flea agents from the group consisting of Imadiclopid, Pyriproxyfen, Fipronil, Methoprene and Permethrin.

As one example, Permethrin, a widely used synthetic pyrethroid, is a water-insoluble potent anti-lice chemical. To encapsulate the Permethrin in halloysite, the micro-tube's lumen was hydrophobized with SDS as described above to enhance loading with hydrophobic Permethrin. The Permethrin is dissolved in acetone at 20 mg/ml and the halloysite-SDS is dispersed in the solution at the same concentration. The dispersion is stirred overnight and then subjected to vacuum and stirring cycles for 30 min and 1 hour respectively three times. The solvents are replenished after every vacuum step (i.e., with acetone without micro-tubes). The solvent is dried off under vacuum after the third cycle and the dried micro-tubes are washed with their solvent and centrifuged at 5000 rpm for 2 min to separate out the excess drug. The washed product is dried under vacuum.

Another example embodiment could utilize the hair drug minoxidil, which has been proven to induce hair growth factors topically and is prescribed as an effective medication against apolecia. Halloysite-SDS and minoxidil are added to methanol at 50 mg/mL each and dispersed through sonication. The dispersion is stirred overnight and then subject to vacuum and stirring cycles for 30 min and 1 hour respectively three times. The solvent is replenished after every vacuum step. The solvent is dried off under vacuum after the third cycle and the dried tubes are washed with their solvent and centrifuged at 5000 rpm for 2 min to separate out the excess drug. The washed product is dried under vacuum.

The present disclosure describes a simple and robust hair surface engineering scheme to immobilize pristine and chemically-modified clay nanotubes onto hair cuticles. Self-assembly of halloysite clay occurs within few minutes and results in formation of a dense 3-5 µm layer of the nanotubes on the hair surface, significantly altering the hair's optical and structural properties. The surface modification of hair with clay nanotubes is very resilient, withstanding up to 10 shampoo washes. The method is universal and works well with both human and animal hair, as tested with human, dog, cat and horse hair. Importantly, halloysite nanotubes, a natural biocompatible material having 10-20% loading capacity (after chemical modification) due to its lumen, with the ability to encapsulate functional molecules (dyes or drugs), renders the hair surface with novel functionalities. Halloysite-based hair dye treatment was effective for coloring of both pigmented and grey hair.

This disclosure also describes a novel approach for topical drug administration using hair surface coating with the nanoclays. Halloysite can be loaded with a wide selection of drugs (e.g., minoxidil), sustaining their gradual slow release; therefore, the assembly of such loaded nanotubes on hair will facilitate the delivery of drugs.

Although the above embodiments describe the dye or biocide loaded micro-tubes being applied to mammal hair, the micro-tubes could also be applied to textiles, including textiles composed of (or "primarily composed of," i.e., at least 51% composed of) cotton, wool, silk, or cellulose fiber coatings. It has been found that cloth fibers coated with unloaded pristine halloysite micro-tubes burn at a rate 80% to 120% slower than the same cloth fibers which are uncoated. And while substantial flame retardance may be achieved with unloaded micro-tubes, there could also be embodiments where flame retardant chemicals are loaded into the micro-tubes. The treatment process for textiles can be similar to the above described hair application techniques. For example, the solvent requirements, concentration of halloysite dispersions and treatment time can be similar to that described above. The micro-tubes could be applied to the textile by immersing the textile in the micro-tube containing aqueous dispersion or possibly by heavily spraying the dispersion onto the textile. In one example, halloysite micro-tubes coated on wool fibers resulted in a halloysite coating which was about 2 wt % of the wool fiber, but in other examples the coating could be between about 0.1 wt % and about 10 wt % (or any sub-range in between) of the textile fabric (including silk). In one instance, it was found that additional coating stability was achieved with a 1 minute treatment in 0.5 wt % polycation (e.g., polyethyleneimine or chitosan) solution, but in other embodiments the concentration of the polycation solution could range between about 0.1% wt % and about 1 wt % together with varying application times (e.g., any time from 30 seconds to 30 minutes). The polycation solution may be applied to the textile while it is still wet from the micro-tube dispersion or after the dispersion has dried on the textile. Likewise, the pH of the dispersion can vary more widely than with hair applications, for example, the pH for the textile application can vary between about 2 and about 12 (or any sub-range in between).

In still further embodiments, the micro-tubes loaded with dyes could be applied to textiles for coloring purposes. The halloysite micro-tubes could be loaded with any number of dyes, with non-limiting examples including: Alcian yellow GXS Alizarin, Alizarin red S, Alizarin yellow GG, Alizarin yellow R, Azophloxin, Bismarck brown R, Bismarck brown Y, Brilliant cresyl blue, Chrysoidine R, Chrysoidine Y Congo red, Crystal violet, Fuchsin acid, Gentian violet, Janus green, Lissamine fast yellow, Martius yellow, Meldola blue, Metanil yellow, Methyl orange, Methyl red, Naphthalene black 12B, Naphthol green B, Naphthol yellow S, Orange G, Rose Bengal, Sudan II, Titan yellow, Tropaeolin O, Tropaeolin OO, Tropaeolin OOO, Victoria blue 4R, Victoria blue B, Victoria blue R, and Xylene cyanol FF.

Figure 3A:
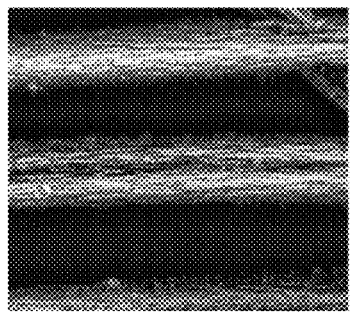
FIG. 3A is an optical confocal profilometer image of pristine 20 μm diameter wool fibers.
Figure 3B:
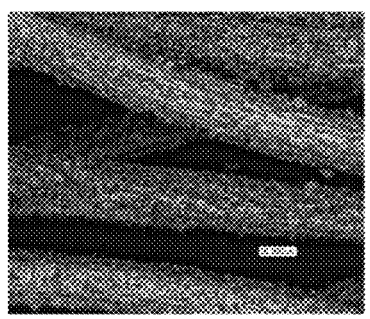
FIG. 3B is an optical confocal profilometer image of halloysite coated 20 μm diameter wool fibers. Micro-tube coating is ca 2 wt % of the wool fiber.
Figure 3C:
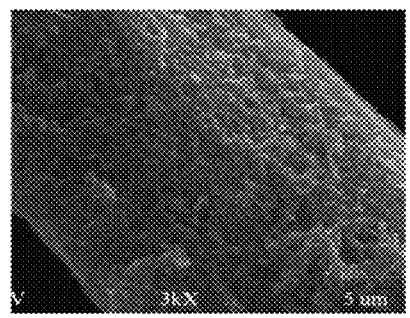
FIG. 3C is a scanning electron microscopy (SEM) image of natural lignocellulose microfiber coated with halloysite.

The micro-tubes would be dispensed in an aqueous carrier liquid having a pH most suitable for the type of textile fiber, e.g., a lower pH for silk and a higher pH for wool. The textile would be immersed in the carrier liquid for a time period ranging from 5 minutes to 30 minutes. The textile would then typically have a polycation solution applied to it in order to stabilize the adherence of the micro-tubes to the fibers of the textile. FIG. 3A is an optical confocal profilometer image of pristine 20 μm diameter wool fibers. FIG. 3B is an optical confocal profilometer image of halloysite coated 20 μm diameter wool fibers. The micro-tube coating is ca 2 wt % of the wool fiber. FIG. 3C is a scanning electron microscopy (SEM) image of natural lignocellulose microfiber coated with halloysite.

The particular embodiments shown herein are by way of example and for purposes of illustrative discussion of certain (sometimes preferred) embodiments of the present disclosure and are presented to assist in understanding the principles and conceptual aspects of various embodiments of the disclosure. In this regard, no attempt is made to show structural details of the disclosure in more detail than is necessary for the fundamental understanding of the disclosure and to allow those skilled in the art to make and use the embodiments without undue experimentation. Further details regarding certain of the disclosed embodiments may be found in A. Panchal, G. I. Fakhrullina, R. F. Fakhrullin, and Y. M. Lvov, "Self-assembly of clay nanotubes on hair surface for medical and cosmetic formulations," Nanoscale, 2018, which is incorporated by reference herein in its entirety.

The term "about" will typically mean a numerical value which is approximate and whose small variation would not significantly affect the practice of the disclosed embodiments. Where a numerical limitation is used, unless indicated otherwise by the context, "about" means the numerical value can vary by +/−5%, +/−10%, or in certain embodiments +/−15%, or even possibly as much as +/−20%. Similarly, "substantially" will typically mean at least 85% to 99% of the characteristic modified by the term. For example, "substantially all" will mean at least 85%, at least 90%, or at least 95%, etc.

The invention claimed is:

1. A biocide mixture for hair comprising:
   (a) a carrier liquid;
   (b) alumino-silicate micro-tubes having a biocide loaded into a lumen of the micro-tubes;
   (c) wherein the micro-tubes are present in the carrier liquid in a concentration of between about 3 mg/ml and about 100 mg/ml; and
   (d) wherein the mixture has a pH of between about 3.5 and about 7.5.

2. The biocide mixture of claim 1, wherein the biocide is a pediculicide.

3. The biocide mixture of claim 2, wherein the pediculicide is one from the group consisting of Permethrin, IR 3535, Saltidin, Picaridin, Cinerin, and N,N-Diethyl-meta-toluamide (DEET).

4. The biocide mixture of claim 1, wherein the biocide is an anti-flea agent.

5. The biocide mixture of claim 4, wherein the anti-flea agent is one from the group consisting of Imadiclopid, Pyriproxyfen, Fipronil, Methoprene and Permethrin.

6. A hair dying kit comprising;
   (a) a first container having a volume of carrier fluid, the carrier fluid having a water content of at least 65%;
   (b) a second container having a weight of alumino-silicate micro-tubes having a hair dye agent loaded into a lumen of the micro-tubes, the second container maintaining the alumino-silicate micro-tubes in a dry state;
  (c) wherein the weight of alumino-silicate micro-tubes to the volume of carrier fluid is between 5 mg/ml and 100 mg/ml.

7. The hair dying kit of claim 6, wherein the hair dye agent is a water soluble dye agent.

8. The hair dying kit of claim 6, wherein the hair dye agent is a water insoluble dye agent.

9. The hair dying kit of claim 6, wherein the hair dye agent loaded into a lumen of the micro-tubes to at least a 4 weight percent dye loading efficiency.

10. The hair dying kit of claim 6, wherein the hair dye agent is one from the group consisting of Shikonin, Quercetin, Lawsone, Isorhamnetin, Curcumin, and Alizarin.

11. The hair dying kit of claim 6, wherein an exterior surface of the micro-tubes have a contact angle of at least about 30°.

12. A method of applying a coloring agent to textiles comprising the step of applying to the textile a coloring mixture for at least one minute, wherein the coloring mixture comprises:
  (a) an aqueous based carrier liquid;
  (b) alumino-silicate micro-tubes having a dye loaded into a lumen of the micro-tubes to at least a 3 weight percent dye loading efficiency;
  (c) wherein the micro-tubes are present in the carrier liquid in a concentration of between about 5 mg/ml and about 100 mg/ml; and
  (d) wherein the mixture has a pH of between about 2 and about 12.

13. The method of applying a coloring agent to textiles according to claim 12, wherein an exterior surface of micro-tubes have a contact angle of at least about 30°.

14. The method of applying a coloring agent to textiles according to claim 12, wherein after application of the micro-tube dispersion, a polycation solution is applied to the textile.

15. The method of applying a coloring agent to textiles according to claim 12, wherein the dye is one from the group consisting of Alcian yellow GXS Alizarin, Alizarin red S, Alizarin yellow GG, Alizarin yellow R, Azophloxin, Bismarck brown R, Bismarck brown Y, Brilliant cresyl blue, Chrysoidine R, Chrysoidine Y Congo red, Crystal violet, Fuchsin acid, Gentian violet, Janus green, Lissamine fast yellow, Martius yellow, Meldola blue, Metanil yellow, Methyl orange, Methyl red, Naphthalene black 12B, Naphthol green B, Naphthol yellow S, Orange G, Rose Bengal, Sudan II, Titan yellow, Tropaeolin O, Tropaeolin OO, Tropaeolin OOO, Victoria blue 4R, Victoria blue B, Victoria blue R, and Xylene cyanol FF.

16. The method of applying a coloring agent to textiles according to claim 12, wherein the textile is primarily formed of one from the group consisting of cotton, wool, silk, or cellulose fiber.

\* \* \* \* \*